US008414126B2

(12) United States Patent
Giraudet et al.

(10) Patent No.: US 8,414,126 B2
(45) Date of Patent: Apr. 9, 2013

(54) EVALUATION AND IMPROVEMENT OF DYNAMIC VISUAL PERCEPTION

(75) Inventors: Guillaume Giraudet, Charenton-le-Pont (FR); Adrien Bak, Charenton-le-Pont (FR)

(73) Assignee: Essilor International (Compagnie Generale d'Optique, Charenton le Pont (FR)

( * ) Notice: Subject to any disclaimer, the term of this patent is extended or adjusted under 35 U.S.C. 154(b) by 0 days.

(21) Appl. No.: 12/920,314

(22) PCT Filed: Feb. 23, 2009

(86) PCT No.: PCT/EP2009/052135
§ 371 (c)(1),
(2), (4) Date: Aug. 30, 2010

(87) PCT Pub. No.: WO2009/106510
PCT Pub. Date: Sep. 3, 2009

(65) Prior Publication Data
US 2011/0001924 A1    Jan. 6, 2011

(30) Foreign Application Priority Data
Feb. 29, 2008    (EP) .................................... 08300127

(51) Int. Cl.
*A61B 3/02*    (2006.01)
*A61B 3/00*    (2006.01)
(52) U.S. Cl. .......................... 351/237; 351/222; 351/246
(58) Field of Classification Search .................. 351/203, 351/222, 224, 237, 246
See application file for complete search history.

(56) References Cited

U.S. PATENT DOCUMENTS

| | | | |
|---|---|---|---|
| 4,611,583 A * | 9/1986 | Wasserman | 606/204.25 |
| 6,213,956 B1 * | 4/2001 | Lawton | 600/558 |
| 6,364,845 B1 | 4/2002 | Duffy et al. | |
| 2003/0109800 A1 | 6/2003 | Polat | |
| 2003/0174284 A1 | 9/2003 | Stewart | |
| 2005/0007550 A1 * | 1/2005 | Turkov et al. | 351/203 |
| 2007/0121066 A1 * | 5/2007 | Nashner | 351/210 |
| 2008/0278682 A1 * | 11/2008 | Huxlin et al. | 351/203 |
| 2010/0128222 A1 * | 5/2010 | Donaldson | 351/210 |

FOREIGN PATENT DOCUMENTS

| | | |
|---|---|---|
| WO | WO 98/22016 | 5/1998 |
| WO | WO 98/44848 | 10/1998 |

OTHER PUBLICATIONS

AAEN-Stockdale et al., "Second-order optic flow processing", Vision Research, Pergamon Press, vol. 47, No. 13, pp. 1798-1808, May 19, 2007.
Simmers et al., "The extent of the dorsal extra-striate deficit in amblyopia", Vision Research, Pergamon Press, vol. 46, No. 16, pp. 2571-2580, Aug. 1, 2006.
Ditchfield et al., "Processing of global form and motion in migraineurs" Vision Research, Pergamon Press, vol. 46, No. 1-2, pp. 141-148, Jan. 1, 2006.
Dickinson et al., "Selectivity for coherence in polar orientation in human form vision", Vision Research, Pergamon Press, vol. 47, No. 24, pp. 3078-3087, Oct. 25, 2007.

* cited by examiner

*Primary Examiner* — Jordan Schwartz
(74) *Attorney, Agent, or Firm* — Cozen O'Connor (57) ABSTRACT

A method for evaluating and/or improving dynamic visual perception of an individual, comprising: a) displaying on a screen (11) a moving pattern (12) having a chosen visual complexity feature (Simp), b) providing a human/machine interface (13, 14) enabling the individual to input a value to indicate the pattern that the individual sees on the screen, c) repeating the preceding steps in order to count the number of successive positive answers imputed at step b), and d1) if the number of successive positive comparisons exceeds a predetermined threshold (S1), increasing (S2) the pattern visual complexity feature of a chosen amount, d2) otherwise, lowering (S7) the pattern visual complexity feature of a chosen amount, e) repeating steps d1) and d2) and lowering (Appl h, S3; S8) the chosen amount each time an alternation between steps d1) and d2) is detected, until a predetermined number (THR) of alternations (Alter) is detected, in order to determine a maximum visual complexity feature (Simp) of patterns that the individual can identify. This maximum visual complexity feature defines a quantitative value of the dynamic visual perception of the individual.

17 Claims, 9 Drawing Sheets

EVALUATION AND IMPROVEMENT OF DYNAMIC VISUAL PERCEPTION

RELATED APPLICATIONS

This is a U.S. national stage of application No. PCT/EP2009/052135, filed on Feb. 23, 2009.

This application claims the priority of European application no. 08300127.1 filed Feb. 29, 2008, the entire content of which is hereby incorporated by reference.

FIELD OF THE INVENTION

The invention relates to a method performed by software means and to a computer system for evaluating and improving the vision of an individual.

More specifically, the invention relates to the field of visual perception and acuity abilities of a person, and to visual perception process and neural performance of a person.

BACKGROUND OF THE INVENTION

Human eyesight is a product of two separate processes that work together to form images for a person to "see". One of these processes, herein referred to as the physical component, concerns the physical structure of the various elements of the eye and how incoming light is treated and processed by the eye. Defects in the shape of the cornea, the retinal wall, or the optic nerve can impair or destroy the functionality of a person's eye and thus impair or eliminate the ability to perceive images. Fortunately, defects in the cornea of a person can be corrected through the use of glasses, contacts, or surgery such as laser keratotomy. Likewise, defects in the retina of a person might be often repairable by surgery.

The second process, enabling humans to see images, is herein referred to as the neurological component. This component concerns neural processing in the brain and how the brain analyzes information sent from the eyes to produce an image. A person can likewise have a number of defects in this component of the visual process, such as reduced visual acuity, reduced sensitivity for spatial contrast, reduced vernier acuity, spatial distortion, abnormal spatial interactions and impaired contour detection.

More particularly, a retina includes three kinds of cells:
photoreceptors (cones and rods) for light detection and transduction in the eye, at a first stage,
bipolar cells for integrating information coming from photoreceptors, at a second stage, and
ganglion cells, performing a pre-processing of the signal to be sent to the brain, at a third stage.

The ganglion cells include two kinds of cells:
so-called "X cells" specifically for detections of low time frequency but high spatial frequency targets (e.g. vision of slow events with accurate details), and
so-called "Y cells" specifically for detections of high time frequency but low spatial frequency targets (e.g. vision of fast events but with few details).

The information given by X cells is treated in the brain by parvocellular neurons (called "P way" or "slow way" hereafter) whereas the information given by Y cells is treated in the brain by magnocellular neurons (called "M way" or "fast way" hereafter).

The P way corresponds to a static vision of fine details, corresponding to a visual perception which is usually evaluated through visual acuity. The M way corresponds, on the opposite, to a less accurate, but dynamic, vision.

However, usually, the visual abilities of an individual are evaluated on the basis of his visual acuity. For example, a selection criterium of an airplane pilot is based on an evaluation of his visual acuity.

Studies have shown that for a movement of a target lower than 30° per second (angular speed), the static visual acuity and the dynamic visual perception were both used to follow the target and to determine its details. However, for a speed of the target upper than 30° per second, the M way and the P way were completely uncorrelated and independent.

Many studies have been carried out on static visual acuity. For example, a method for identifying deficiencies and/or inefficiencies in neuronal interaction of a person's visual cortex and possibly train this person for improving his visual acuity performance has been proposed by the Company Neurovision Inc. (Singapore) to offer eye correction training session.

Although clinical tests have shown that about 70 percent of the users of training such as a Neurovision® training system and method have improved their eye conditions, it appears that the efficiency of the method is not optimal for dynamic visual perception.

Accordingly there remains a need for evaluating and improving the dynamic visual perception.

SUMMARY OF THE INVENTION

Embodiments of the present invention aim to improve the situation.

To this end, according to a first aspect of the invention, there is provided a method implemented by computer means, for evaluating a dynamic visual perception of an individual, comprising at least the steps of
a) displaying on a screen at least one moving pattern having a chosen visual complexity feature, said pattern being selected (for example randomly), amongst a plurality of possible patterns having each a value,
b) providing a human/machine interface enabling the individual to input a value to indicate the pattern that the individual sees on the screen,
c) receiving through said human/machine interface the inputted value and comparing said inputted value to the value of the displayed pattern,
d) repeating the preceding steps in order to count the number of successive positive comparisons at step c), and
   d1) if the number of successive positive comparisons exceeds a predetermined threshold, increasing said pattern visual complexity feature of a chosen amount,
   d2) otherwise, lowering said pattern visual complexity feature of a chosen amount,
e) repeating step d) and lowering said chosen amount each time an alternation between steps d1) and d2) is detected, until a predetermined number of alternations is detected, in order to determine a maximum visual complexity feature of patterns that the individual can identify, said maximum visual complexity feature defining a quantitative value of the dynamic visual perception of the individual.

In an embodiment, steps d) and e) may be implemented in the form of a so-called "staircase", as it will be described in details below. It is important to note here that the displayed patterns to be recognized are moving during the tests of the staircase.

Methods according to embodiments of the invention may be performed for evaluating the dynamic visual perception but the inventors have observed however that displaying moving patterns on a screen sufficed to improve yet the dynamic visual perception (DVP) of the individual seeing the patterns.

More particularly, it has been observed that training sessions during which selected moving patterns were displayed enabled to improve individuals DVP and, most of all, the lower the initially evaluated DVP was, the higher the improvement of the DVP was thanks to the training sessions. A method for improving the DVP can, for example, aim to rest the eyes and eliminate a tiredness of the individual.

Thus, according to a second aspect of the invention, a method implemented by computer means, is provided for improving a dynamic visual perception of an individual. Embodiments of the method according to the second aspect comprise at least a step of displaying on a screen at least one moving pattern having a chosen visual complexity feature, said pattern being selected amongst a plurality of predetermined patterns. More particularly, in order to improve progressively the dynamic visual perception of the individual, the method further comprises an evaluation of the individual's dynamic visual perception, as described above, for improving said perception. Of course, the level of difficulty of a training session will be increased as a function of the evaluated DVP at the end of a preceding session, for example.

Therefore, as the aforesaid pattern maximum visual complexity in the evaluation method defines an individual's DVP level, step e) of the evaluation method can be carried out several times to observe a progressive increase of said pattern maximum visual complexity on the individual. In an embodiment, this increase of the visual complexity can define quantitatively a level of improvement of the individual's dynamic visual perception.

In another embodiment, an increasing function of an amount of individual's good answers probability versus a test simplicity parameter is determined. This function comprises:
  a first asymptote of zero value probability of good answers given at a test simplicity parameter below a threshold value corresponding to the aforesaid pattern maximum visual complexity,
  and a second asymptote of 100% value probability of good answers given at a test simplicity parameter greater than the test simplicity parameter threshold.

Here, an integral value of the function is preferably calculated and step e) of the evaluation method is carried out several times to observe an increase of the integral value on said individual. More particularly, the integral value increase can define quantitatively an improvement of the individual's dynamic visual perception.

The method for improving the individual's DVP or the method for evaluating the individual's DVP can be both carried out on at least one eye of the individual, in order to improve or to test selectively the dynamic visual perception of the trained or tested individual's eye.

In an embodiment, the evaluation or the improvement of an individual's DVP can be based on at least one element amongst:
  an ability to identify a moving pattern with eye tracking,
  an ability to identify a moving pattern without eye tracking,
  an ability to identify a global movement of a plurality of moving patterns,
  an ability to read a chosen text displayed on the screen.

In an embodiment advantageous for evaluating the individual's DVP, the displayed patterns may include alphabetic letters to be recognized by the individual, and the pattern visual complexity feature can be thus related to a global size of the alphabetic letters.

In an embodiment rather advantageous for improving the individual's DVP, the displayed patterns include Gabor patches having several possible orientations to be recognized by the individual, and the pattern visual complexity feature can be defined thus by setting at least the amplitude and/or a spatial frequency of the Gabor patches.

In an advantageous embodiment aiming to provide the solution of the invention to a wide range of people, the moving patterns are intended to be displayed on an LCD screen of a portable device (such as a portable gaming device, a cellular phone or a personal digital assistant). However, the quality of a display of Gabor patches on an LCD screen (having a poor resolution) is not optimal. It has been observed, nevertheless, that displaying simple optotypes such as letters of the alphabet can provide equivalent results and is more adapted to LCD small screens (7 inches or less). Therefore, a preferred embodiment may consist on choosing a display of alphabetic letters when the invention is performed on portable devices provided with small screens (having a poor resolution like small LCD screens).

Moreover, randomly moving dots can be added to be further displayed on the screen in order to increase visual complexity. In this embodiment, the display of randomly moving dots can have a dynamic visual effect of a sandstorm where each dot would represent a grain of sand.

For evaluating the ability to identify a moving pattern with eye tracking, in the method for improving the individual's DVP or in the method for evaluating the individual's DVP, the individual is asked to:
  follow the pattern on the screen while the pattern moves randomly from a position of the screen to another a predetermined number of times, for example 9 times,
  and to enter through the computer interface the value of the randomly moving seen pattern.

For example, the pattern may remain steady at each position during a predetermined duration (for example during 180 ms).

In embodiments of the method for improving the individual's DVP or in the method for evaluating the individual's DVP, in order to test or to improve the individual's ability to identify a moving pattern without eye tracking, a fixed pattern (such as a cross) is further displayed on the screen (for example in the middle of the screen), and the individual is asked to stare at the fixed pattern while first and second patterns (such as alphabetic letters or Gabor patches) are displayed and move towards opposite directions on both sides of the fixed pattern. Thus, the individual is asked to input through the computer interface at least one value of the aforesaid first and second moving patterns.

In embodiments of the method for improving the individual's DVP or in the method for evaluating the individual's DVP, in order to test or to improve an ability to identify a global movement of a plurality of moving patterns, a plurality of same moving patterns are displayed on the screen and a predetermined proportion of those same patterns move towards a same direction. Thus, the individual is asked to determine through the computer interface whether at least some of the moving patterns move in a same direction or not. Here, the aforesaid pattern visual complexity may be defined by a complementary value of the proportion of patterns moving in a same direction.

There is also provided a computer system for evaluating or improving a dynamic visual perception of an individual, and including means for performing a method according to the first aspect for evaluation the individual's DVP and/or for improving the individual's DVP.

There is also provided a software product adapted to be stored in a memory of a processor unit of such a computer system, or in a removable memory medium adapted to cooperate with a reader of the processor unit, and/or downloadable from a distant website through an extended network. The software product includes more particularly instructions for implementing a method according to the second aspect for improving the individual's DVP and/or the method for evaluating the individual's DVP.

BRIEF DESCRIPTION OF THE DRAWINGS

FIG. 6 shows an embodiment of the display of FIG. 5, FIGS. 7 and 8 show a display of moving patterns for evaluating the individual's ability to detect a coherent motion (completely incoherent in FIG. 7 and completely coherent in FIG. 8)

DETAILED DESCRIPTION OF EMBODIMENTS OF THE INVENTION

Figure 1:
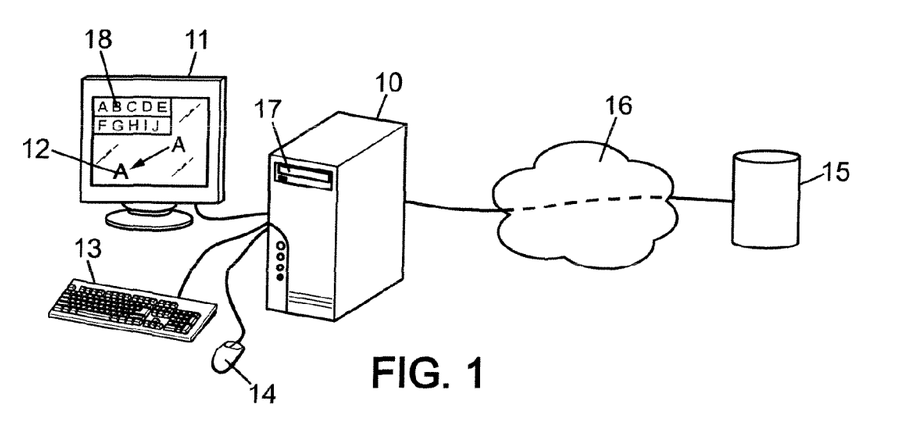
FIG. 1 shows schematically a computer system for implementing methods according to embodiments of the invention.

With reference to FIG. 1, a computer system according to the invention may comprise, for example:
a screen 11 for displaying moving patterns 12;
a human/machine interface enabling a user to input a value corresponding to the pattern that the user sees on the screen;
a central processing unit 10 comprising a memory for storing at least a part of the instructions of a code of a computer program product according to embodiments of the invention.

The human/machine interface may be a keyboard 13 for inputting a value of a pattern recognized by the user. It may be also a mouse 14 for selecting a value displayed on a part 18 of the screen, said part of the screen 18 being provided to that end.

The aforesaid memory for storing the instructions of the program according to embodiment of the invention can be a volatile memory (for example a RAM memory). In this embodiment, the computer may have a communication interface with a server 15, via a network 16 (such as the Internet). Then, the program according to embodiments of the invention can be stored and run by the server 15 and instructions for displaying patterns are sent from the server 15 to the central unit 10, and answers inputted by the user are sent from the computer 10 to the server 15, enabling the server 15 to evaluate or to enhance the level of dynamic visual perception of the user. For example, an applet may be sent by the server 15, first, and be run on the central unit 10, to detect the features of the screen 11 and of a graphic interface included in the central unit 10, enabling thus an adaptation of the patterns to be displayed later (adaptation of the size, as a number of pixels, for example).

In another embodiment, the computer program product according to the invention can be stored in a non-volatile memory of the central unit 10 (such as a ROM memory). In that case, the program is run directly by the computer 10 for evaluating or enhancing the dynamic visual perception of the user.

The computer program product according to the invention can be stored also on a readable medium, such as a CD-ROM, a DVD-ROM, an USB-key, etc. A reader 17 of the medium included in the central unit 10 can read the instructions of the program according to the invention and a processor of the central unit 10 can run those instructions. Thus, the present invention aims also a readable medium which stores instructions of a code of a computer program according to the invention.

It is to be noted that a person (for example an eye-care professional), different from the user, may use the human/machine interface for inputting the values of the patterns recognized by the user to evaluate or enhance his dynamic visual acuity.

Figure 2:
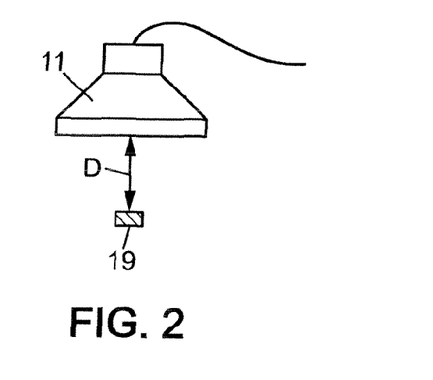
FIG. 2 shows schematically further elements of the installation of FIG. 1.

Preferably, with reference to FIG. 2, the head of the individual is held on a chin support 19 located at a distance D from the screen 11. The distance D is chosen according to the apparent size of a pixel zone of the screen, to be considered by the individual as a point on the screen 11. For example, if a visualisation zone of the screen is a square of 800×800 pixels centred on the screen and D=0.7 m, a pixel is seen under an angle of 0.03° and this is just inferior or equal to a resolution ability of an individual, such that this square of 800×800 pixels can be considered as a point.

Figure 3:
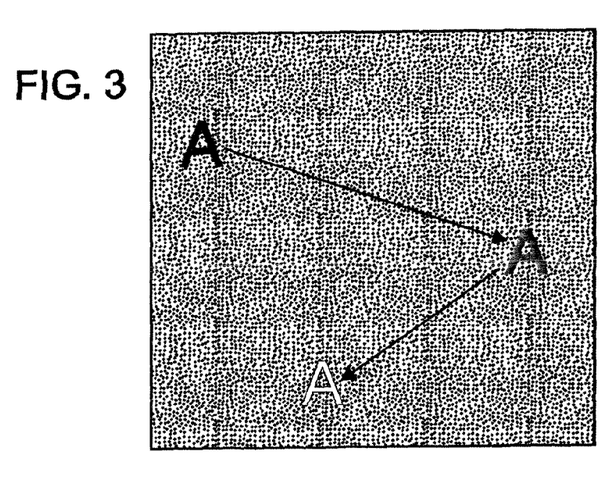
FIG. 3 shows the display of a moving pattern in a non limiting example used in an embodiment of the evaluation method according to the invention.

In the method for evaluating the individual's DVP, the pattern displayed on the screen 11 can be a moving optotype, for example an alphanumeric letter. A test can consist in recognizing the letter moving randomly on the screen. The luminosity of the moving pattern increases during its movement. As shown in FIG. 3, the patterns are preferably displayed with a light color on a dark colored background.

For example, during a test, the letter explores nine different positions of the screen and stays on each position during 180 ms. Its luminance varies linearly from 11% to 99% of the maximal screen luminance. After displaying the pattern in its last position, the computer asks the individual (for example by the way of a written message on the screen) to determine which letter was displayed. The individual may press on a letter of the keyboard 13 to answer or can orally answer if a microphone plugged to the computer is provided.

In a next test, another letter, for example randomly selected among the 26 letters of the Latin alphabet, can be displayed again within the same conditions, or can be displayed while the simplicity (or the difficulty) of the test has varied. As for example, a simplicity of the tests (noted "Simp" hereafter) can be linked to the size of the letter, in pixels, according to a relationship of the type: Size=25*Simp+4, corresponding to an angular size given by Size=0.75*Simp+0.12 (in degrees).

It will be referred hereafter to simplicity criteria (rather than complexity). However, same principles apply for complexity criteria, being understood that an increase (respectively a decrease) of complexity represents a decrease (respectively an increase) of simplicity. Hereafter, a task is defined as a set of tests whose difficulty varies. Moreover, an individual's answer describing the observed pattern is considered positive (respectively negative) if it matches (does not match) the displayed pattern.

More particularly, each task is composed of a sequence of tests. The complexity (or the simplicity) of the tests is adapted according to the individual's answers in real time. The individual is asked to determine a specific feature of the displayed pattern and his answer is processed to adapt the complexity (or the simplicity) of the next test to his dynamic acuity level.

Preferably, a warning message is displayed on the screen at the beginning of each test to focus the individual's attention on the test.

A VDP evaluating algorithm preferably controls simplicity through a task, in the form of an adaptive staircase method as described below, with reference to FIG. 4. In the example given in FIG. 4, the level of simplicity Simp is supposed to be maximum, at step S0. The first step S1 corresponds to the following test:

"has the individual correctly identified n successive moving patterns?" or, equivalently, "has the individual correctly answered to n successive tests?"

If the response is "yes" (arrow Y at the output of step S1), then the simplicity can be lowered, and mathematically the value Simp is decreased by a chosen value X (an example of which will be given hereafter). As far as the response is "yes" (arrow Y at the output of step S1), the value Simp can be decreased by the value X (for example p times such that Simp=1−pX, if the simplicity is evaluated in a scale from 0 to 1). However, the simplicity value Simp is chosen to be not lower than a threshold value Smin (with for example Smin=0).

If it occurs that the individual gives at least one bad answer among n successive answers (arrow N at the output of step S1), then, the following steps are performed:

in step S3, the value X is lowered (for example multiplied by a positive factor h which is inferior to 1, such that X becomes hX) and a number of alternations between n successive positive tests and m successive negative tests is counted and incremented (e.g. the number of responses N to test S1 or to test S6 described below), in step S4, if the number of alternations exceeds a threshold THR, then the task is finished and the final value found for the simplicity Simp is outputted (step S5).

Step S6 corresponds to the following test:

"has the individual failed to identify m successive moving patterns?" or, equivalently, "has the individual given m successive wrong answers?"

If the response is "yes" (arrow Y at the output of step S6), then the simplicity can be increased, and mathematically the value Simp is increased by the previous value X multiplied by the factor h. It will be understood thus that at each "alternation" (or answer N to step S1 or S6), the value X is lowered.

It can be preferred to limit the value X to a chosen minimum value (for example Xmin=0.1). As far as the response is "yes" (arrow Y at the output of step S1), the value Simp can be decreased by the same value X (without lowering X by the multiplication by the factor h).

If it occurs that the individual gives at least one good answer among m successive answers (arrow N at the output of step S6), then, the following steps are performed:

in step S8, the value X is lowered (by multiplication by the factor h) and the number of alternations "Alter" is counted and incremented, in step S9, if the number of alternations exceeds the threshold THR, then the task is finished and the final value found for the simplicity Simp is outputted (step S10).

The task may be ended if a predetermined number of alternations, in the whole, is reached or if a predetermined number of successive alternations between n good answers and m wrong answers is reached.

Figure 4:
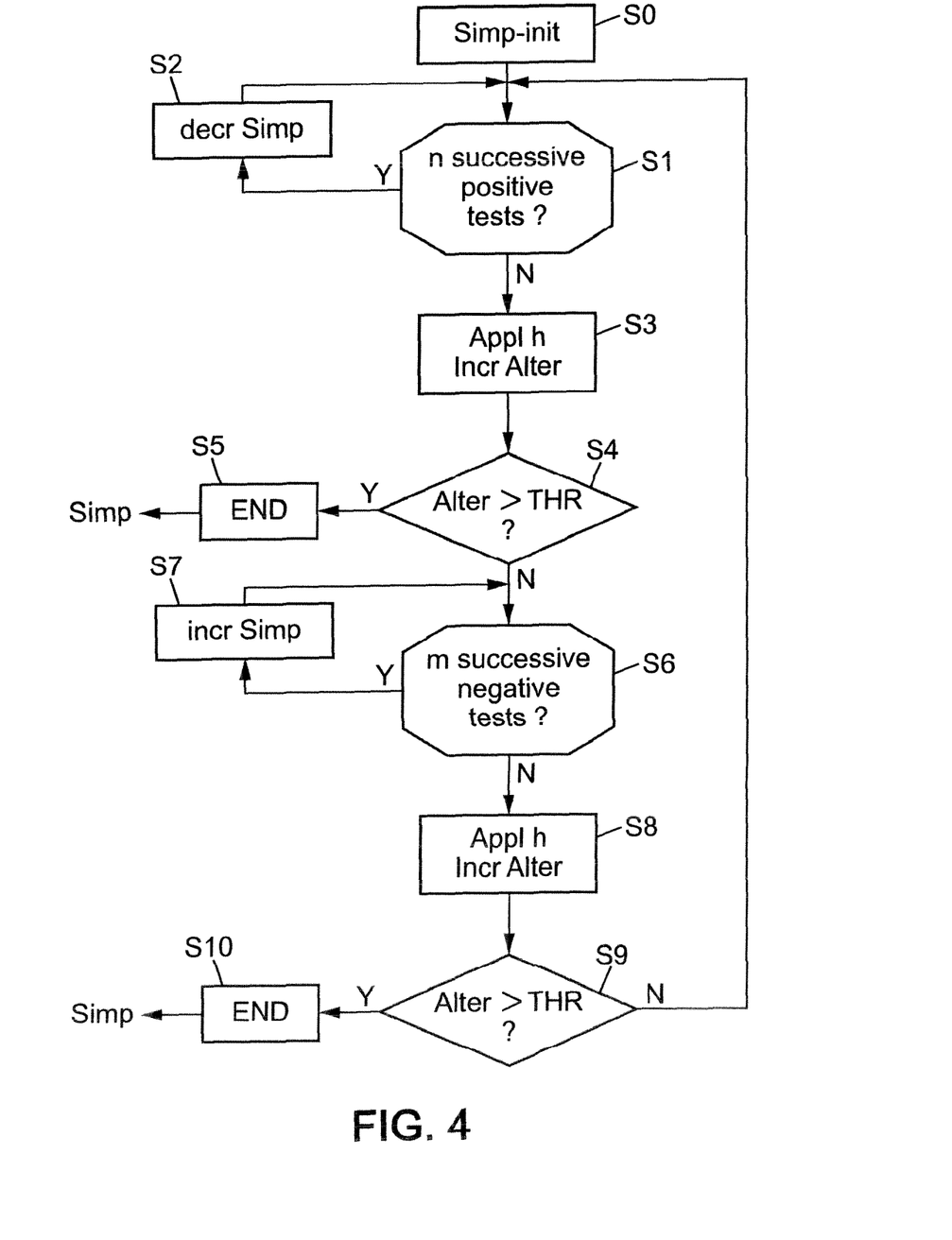
FIG. 4 shows an example of a staircase method which can be used in an embodiment of the evaluation method of the invention.

The example given with reference to FIG. 4 is related to a staircase said "m up-n down" (with n>m since the initial simplicity is maximum at the beginning of the task).

In the application of the staircase method in the background of the invention, a "1up-3down" staircase has given satisfactory results.

For the task aiming successive tests consisting on recognizing a moving pattern with eye tracking, as shown in FIG. 3, the parameters of the staircase are for example:

a minimum simplicity Smin=0 (in a scale from 0 to 1),
a maximum simplicity Smax=1 (in a scale from 0 to 1),
an initial simplicity at a beginning of the test S0=Smax=1 (e.g. the first task begins with a maximum simplicity),
the value X being set first at X0=0.5,
the factor h=0.3,
the minimum value of X being Xmin=0.1.

The task is ended for a total number of alternations Alter=17 and/or if a number of successive alternations is Ac=4.

Figure 5:
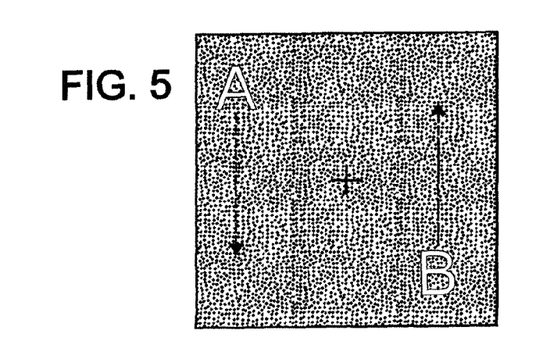
FIG. 5 shows a display of moving patterns for evaluating the individual's DVP without eye tracking.

FIG. 5 shows an example for testing the individual's ability to identify a moving pattern without eye tracking. It is asked to the individual to perceive patterns around a point where he focuses his sight. The individual is asked to stare at a fixed pattern (the cross in the example of FIG. 5) while two other patterns are displayed and move towards opposite directions on both sides of the cross. These two patterns may be two optotypes, for example two letters, having a rectilinear uniform movement of opposite direction on both sides of the focusing cross target. In the example given in FIG. 6, eight possible pairs of trajectories can be randomly chosen for the display. The individual is asked to determine which letters are displayed. For example, the letters movement lasts 90 frames of 10 ms each and the luminance increases linearly through the display. The term "frame" aims here the fact that, the letters moving from a place of the screen to another, they remain steady at each place during a so-called "frame" of 10 ms for example.

Figure 6:
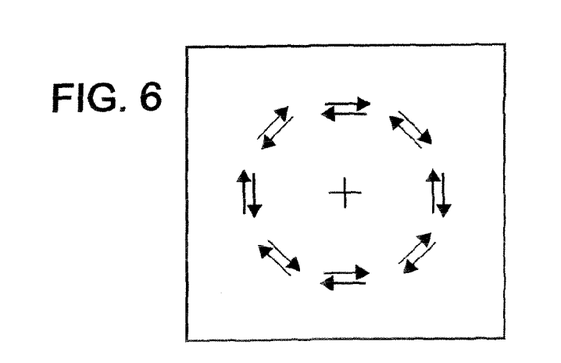

In this kind of task for evaluating DVP without eye tracking, a simplicity value Simp can be linked again to the size of the letters, given in pixels, according to the relation:

$$Size=30*Simp+8.$$

For example, the algorithm for evaluating DVP without eye tracking can be an adaptive staircase in the form again of "1up-3down" as described above, with the following parameters:

Smin=0 (in a scale from 0 to 1),
Smax=1,
S0=Smax=1,
X0=0.5,
h=0.2,
Xmin=0.12.

The task is ended for a total number of alternations Alter=12 and/or if a number of successive alternations is Ac=6.

Figure 7:
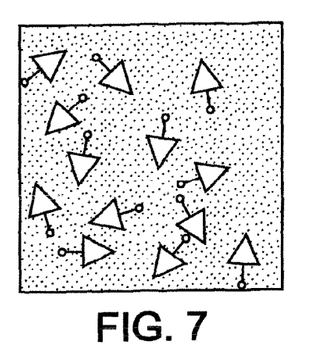
Figure 8:
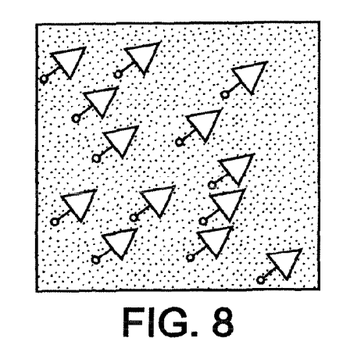

FIGS. 7 and 8 shows an example of test being used for testing the ability of the individual to detect a coherent motion embedded in a moving noise also referred as the ability to "identify a global movement of a plurality of same moving patterns". Two displays of moving dots are shown to the individual. Each display is composed of 300 white dots on a black background. All the dots have the same instantaneous speed value, for example:

$$V=8 \text{ pixels/frame}$$

On one display, dots are moving completely randomly, without any correlation. On the other display, dots motion is partially coherent, meaning that at least a part of the dots are moving toward the same direction. It is added here that the coherently moving patterns are not the same ones from a frame to another. The set of coherently moving patterns is preferably "re-sampled" from a frame to another.

The display lasts preferably 50 frames of 50 ms each and the interval between two stimuli is 250 ms.

FIG. 7 shows the instantaneous speed vectors of the dots for an incoherent movement and FIG. 8 shows the instantaneous speed vectors of the dots for a totally coherent movement. In FIGS. 7 and 8, arrows only of the dots motion vectors are shown.

The individual is compelled to give an answer about which display has a coherent movement.

In this example, test simplicity is linked to the proportion of dots moving in the same direction. The DVP evaluation is based again on an adaptive staircase 1up-3down, with the initial parameters:
Smin=0.01,
Smax=1,
S0=0.4,
X0=0.2,
h=0.3,
S0=0.05,
Alter=10 and Ac=3.

Another task can consist in reading a "difficult" text (e.g. with unusual syntax and vocabulary) in order to avoid any memory effect. The criteria of simplicity can be related here to the time taken for reading a predetermined number of words of the aforesaid text.

All the letters of those tests are preferably given in a typography called "Arial".

Figure 9:
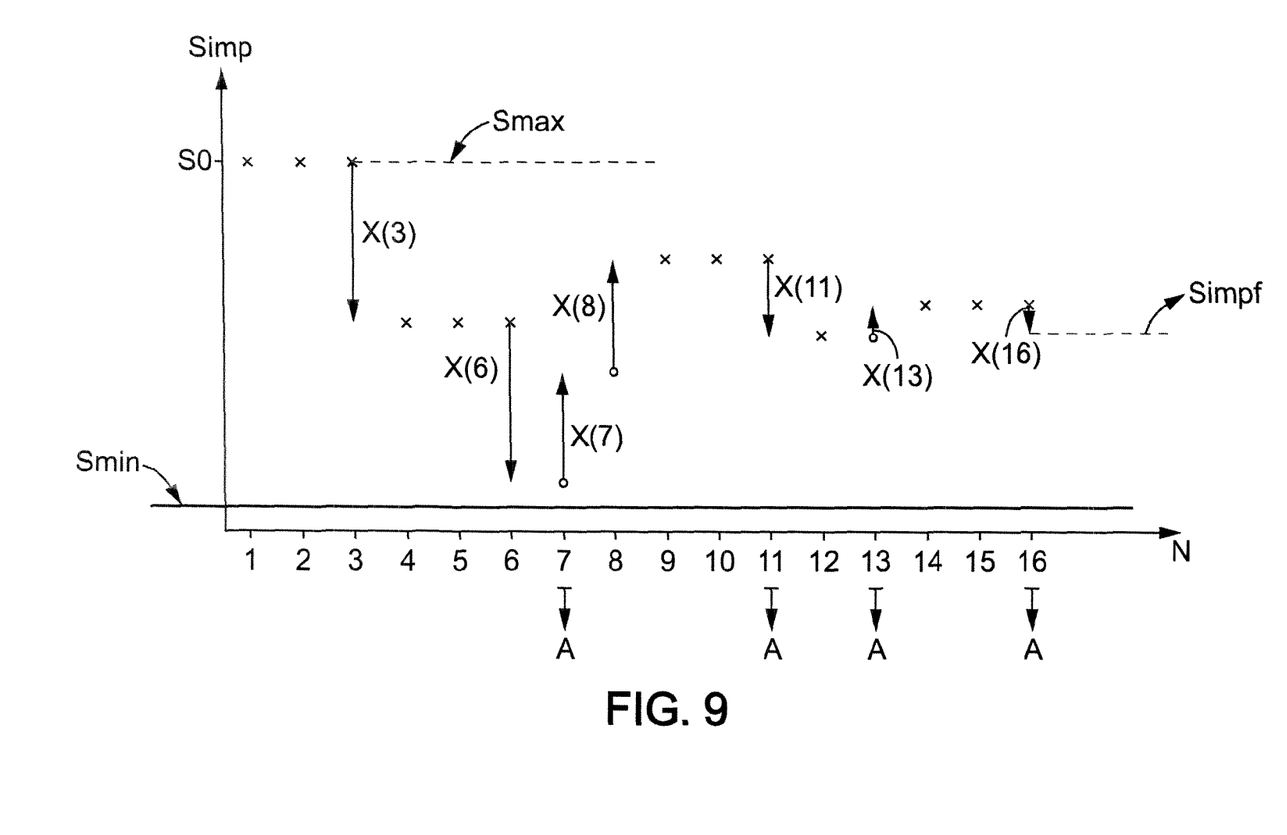
FIG. 9 shows the variations of simplicity in an example of 1up-3down staircase.

It is explained now, with reference to FIG. 9, how the individual's answers are processed during a task, involving a staircase 1up-3down, in order to determine:
the modifications to apply to the simplicity value Simp through the task, in real time,
and, finally, the reached simplicity value Simpf determined at the end of the task, defining a level of the individual's dynamic visual perception, related to this task.

A(N) represents the individual's answer to a test number N on a moving pattern of simplicity Simp(N). For a given simplicity Simp(N) and an answer A(N), it has to be decided whether the task has to be ended or if an additional test N+1 has to be implemented, and in this case, the simplicity value Simp(N+1) has to be determined.

The simplicity is increased of a quantity X if the individual gives a wrong answer to a test and decreased of a quantity X if the individual gives three consecutive positive answers to a test. Simplicity can be adapted within a range determined by initial parameters Smin and Smax. The quantity X depends itself on the good or wrong answers of the individual.

A simplicity alternation is defined as an increase (respectively a decrease) of simplicity that is following, immediately or not, a decrease (respectively an increase) of simplicity. The alternations are noted "A" on FIG. 9. Crosses represent successes and rounds are used for failures.

In the example of FIG. 9, the individual gave 3 successive good answers at N=1, 2, 3. Therefore, the simplicity Simp is decreased by a quantity X(3)=T, such that:

$$\text{Simp}(3)=S0-X(3), \text{ or equivalently: Simp=Smax}-T.$$

Then, the individual gave 3 successive good answers again at N=4, 5, 6. Therefore, the simplicity Simp is decreased again by the same quantity X(6)=X(3)=T, since no alternation occurred for the moment.

$$\text{Thus, the simplicity is given by Simp}(6)=\text{Simp}(3)-X(6)=\text{Smax}-2T.$$

Then, the individual gave 1 wrong answer at N=7. Therefore, the simplicity Simp is increased by a new quantity X(7)=h.X(6)=hT. In fact, since an alternation occurred between the last 3 successive good answers at N=6 and the new wrong answer at N=7, the factor h (inferior to 1) intervene to be multiplied to the latest value X of the simplicity increase or decrease (here a decrease).

$$\text{Thus, the simplicity is given by Simp}(7)=\text{Simp}(6)+X(7)=\text{Smax}-2T+hT.$$

Then, the individual gave 1 wrong answer again at N=8. Therefore, the simplicity Simp is increased again by a quantity X(8)=X(7) (since no alternation occurred between N=7 and N=8).

$$\text{Thus, the simplicity is given by Simp}(8)=\text{Simp}(7)+X(8)=\text{Smax}-2T+2hT.$$

Then, the individual gave 3 successive good answers at N=9, 10 and 11. Therefore, the simplicity Simp is decreased again by a quantity X(11)=h.X(8) (since an alternation occurred between N=8 and N=11),
e.g. $X(11)=h.X(8)=h.X(7)=h^2X(6)=h^2T$.

Thus, the simplicity is given by:

$$\text{Simp}(11)=\text{Simp}(8)-X(11)=\text{Smax}-2T+2hT-h^2T$$

Then, the individual gave 1 good answer (N=12) but failed to give 3 successive good answers and, in particular, gave a wrong answer at N=13. Therefore, the simplicity Simp is increased by a quantity $X(13)=h.X(11)=h^2.X(8)=h^3T$.

Thus, the simplicity is given by:

$$\text{Simp}(13)=\text{Simp}(11)+X(13)=\text{Smax}-2T+2hT-h^2T+h^3T$$

Then, the individual gave 3 successive good answers at N=14, 15 and 16. Therefore, the simplicity Simp can be decreased again by a quantity:

$$X(16)=h.X(13)=h^2.X(11)=h^3.X(8)=h^4T.$$

However, here, it is found that $h^4T$ is lower than a predetermined threshold Xmin and it is preferred to set X(16) at Xmin.

Thus, the simplicity is given by:

$$\text{Simp}(16)=\text{Simp}(13)-X(16)=\text{Smax}-2T+2hT-h^2T+h^3T-X\text{min}$$

In this example, it is chosen to end the staircase after three consecutive alternations (Ac=3). The final simplicity is thus given by the value Simpf=Simp(16). It characterizes a level of dynamic visual acuity of the individual.

Figure 10A:
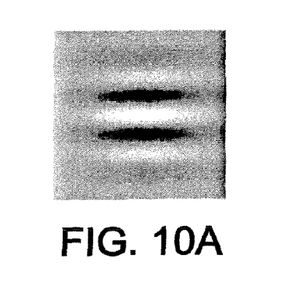
FIGS. 10A and 10B show Gabor patches having respective different spatial frequencies.
Figure 10B:
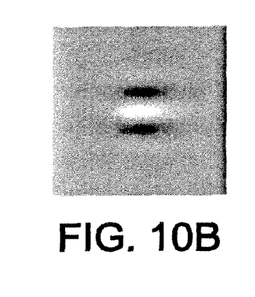
Figure 11A:
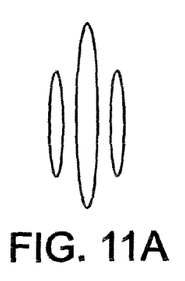
FIG. 11A to 11D show Gabor patches having different respective orientations.
Figure 11B:
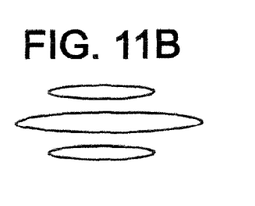
Figure 11C:
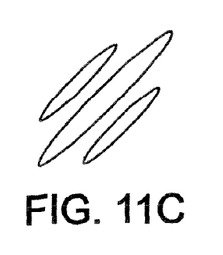
Figure 11D:
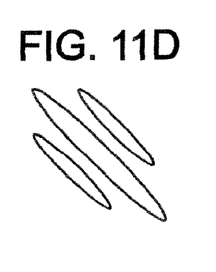

A DVP improving method is described hereafter. It can be constituted of 8 sequences (spaced by an interval of two days, for example), each sequence being divided in two tasks. The first task of the training sessions consists on tests for recognizing an optotype without eye tracking and the second task consists on tests for recognizing an optotype with eye tracking. The optotype is a Gabor patch, as shown in FIGS. 10A and 10B. It includes a succession of dark and light fringes along a given direction. With reference to FIGS. 11A to 11D, four directions are possible. The contrast between the fringes can be set according to a chosen level of simplicity. Moreover, the relative distance between the fringes is given by the spatial frequency value via $k_x$ and $k_y$ in the Gabor function:

$$G(x, y) = A_0 \exp\left[\frac{(x-x_0)^2 + (y-y_0)^2}{\sigma_0^2}\right] \sin[2\pi\omega(\vec{k}_x \cdot x + \vec{k}_y \cdot y)]$$

In the example given in FIG. 10A, the spatial frequency (in at least one direction x) is slightly lower than in the Gabor patch shown in FIG. 10B. Thus, the spatial frequency of the Gabor patches can define a level of simplicity of the tests. An implementation of this embodiment will be described below.

However, preferably, the amplitude Amp of the Gabor patches varies also with the simplicity, according to a relationship of the type:

$$\text{Amp} = Simp \times \sin(\vec{k}, \vec{r}) \exp\left[-\frac{(\vec{r} - \vec{r}_0)^2}{2\sigma^2}\right]$$

The simplicity of each task is determined:
by the results of the DVP evaluation on the individual, initially, on the one hand,
and by the evolution of the training sessions as it will be described below, on the other hand.

It has been observed indeed that, in visual stimulations, the Gabor patch efficiently activates and matches the shape of receptive field in the visual cortex. Contrast sensitivity of adult human subjects at low levels could be increased by a factor of 2 through specific control of the Gabor patches parameters.

The stimuli parameters can be automatically tailored to each subject's abilities. Among these parameters are spatial frequencies, contrast level or amplitude Amp, orientation (e.g. directions of the patches as shown in FIGS. 11A to 11D), etc. Neurones in human vision system are specialised for certain directions and frequencies. Thus, modifying frequency and direction of Gabor patterns enable to assess different neurone groups and to improve DVP evaluation efficiency.

Each session may be designed to train, directly and selectively, dynamic visual ability in the visual cortex. At each session an algorithm may analyze the patient's responses and accordingly adjusts the level of visual difficulty to the range most effective for further improvement. Between sessions, the progress of the patient may be measured and taken into account by the algorithm for the next session. Thus, for each subject an individual training schedule may be designed, and adapted during the training session, based on the initial state of visual performance, severity of dysfunction and progress in training.

Figure 12:
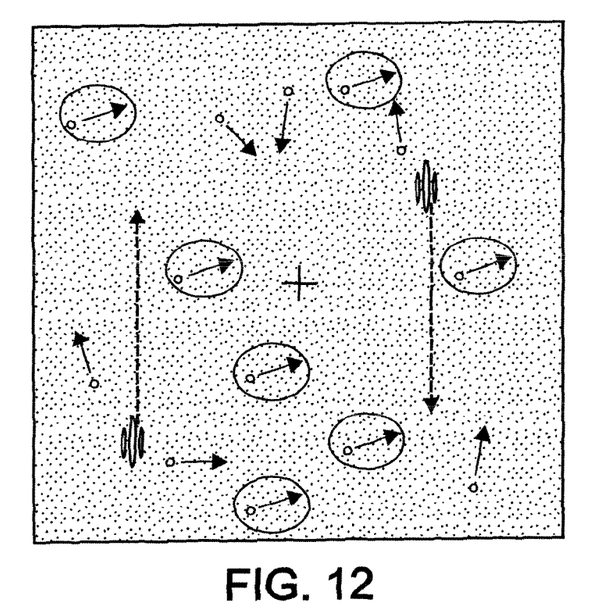
FIG. 12 shows a non limiting example of a display during a task without eye tracking in an embodiment of the DVP improving method according to the invention.

With reference to FIG. 12, the first task, without eye tracking, consists on tests for recognizing the orientation of Gabor patches (among four possibilities as shown in FIGS. 11A to 11D). In the first task, the subject is asked to stare at a fixed cross in the middle of the screen, while two Gabor patches are displayed and move toward opposite directions on both sides of the fixed cross. Moreover, in order to increase difficulty, here, randomly moving dots are added to the display. More precisely, some of the dots are moving coherently in a same direction and, further, the ratio of the coherent dots motion (noted hereafter "RCDM") decreases from the beginning of the tests to the end of the tests of a same session.

In FIG. 12:
the movement of the two Gabor patches is indicated by the two dashed line arrows (which, of course, are not displayed actually to the individual),
partially random movements of the dots are indicated by small arrows (which, of course, are not displayed actually to the individual),
dots moving in a same direction are indicated by an ellipse surrounding them.

These ellipses, of course, are not displayed actually to the individual: only the Gabor patches, the fixed cross and the dots are displayed.

Here, the subject is asked to indicate the orientation of at least one Gabor patch (or of the two Gabor patches). In an embodiment, the two Gabor patches have the same orientation.

Preferably, a staircase task structure is kept in the DVP improving method. Indeed, a staircase structure enables:
a duration of a session which is sufficiently stable, from a session to another, and
an interesting training protocol for the individual.

In an example, a 1up-3down staircase is performed, with the following parameters:
S0=3,
Smax=4 (it is to be noticed that it is different from the initial simplicity S0),
Smin=0.2,
X(0)=1.6,
h=0.5,
Xmin=0.025, and
the total number of alternations Alter ends here the task, with Alter=26.

The duration of a frame is 25 ms. A Gabor patch moves at a speed of 10 pixels per frame.

Figure 13:
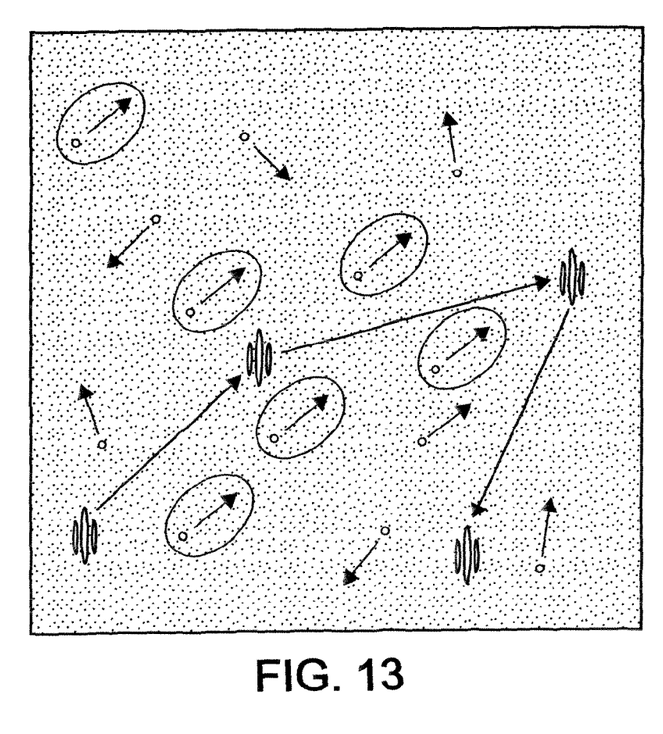
FIG. 13 shows a non limiting example of a display during a task with eye tracking in an embodiment of the DVP improving method according to the invention.

FIG. 13 shows now a display used in the second task to improve DVP with eye tracking. A single Gabor patch randomly moves. The individual is asked to indicate its orientation. Moving dots are further displayed on the screen to increase visual complexity. A 1up-3down staircase is carried out again, with the following parameters:
S0=3,
Smax=4 (it is to be noticed that it is different from the initial simplicity S0),
Smin=0.2,
X(0)=1.0,
h=0.7,
Xmin=0.025, and
the total number of alternations ends the task, with Alter=24.

The Gabor patch moves 6 times from a random position to another and remains steady at each position during 25 ms.

Figure 14:
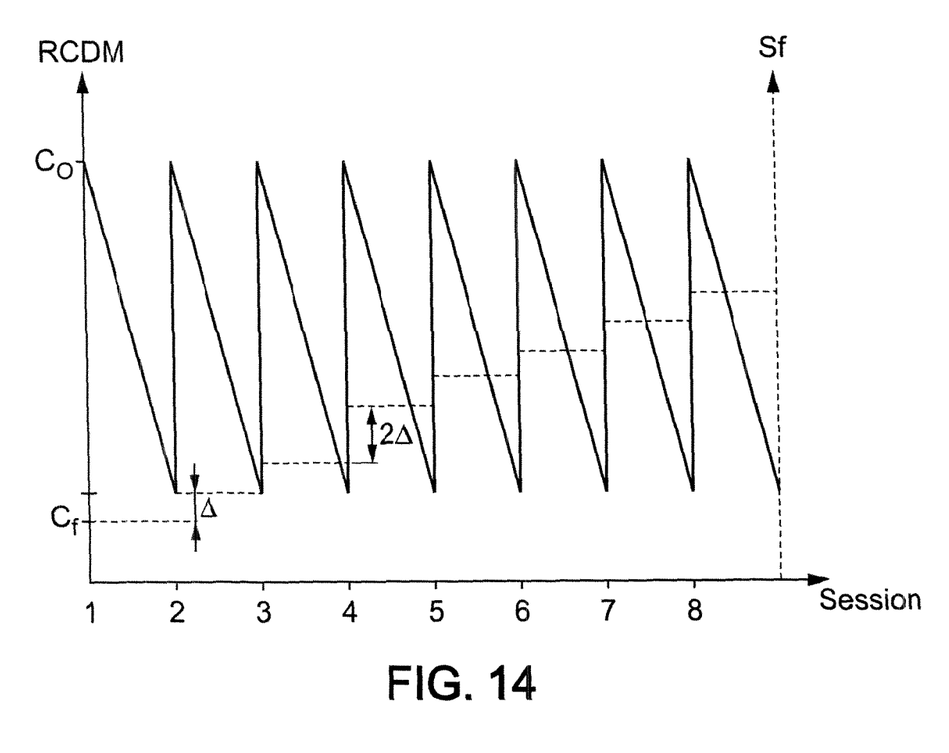
FIG. 14 shows an example for varying a ratio of coherently moving dots in displays of FIGS. 12 and 13, in a same session and for varying the spatial frequency of the Gabor patches in displays of FIGS. 12 and 13 from a session to another (dashed lines)

The ratio of the randomly moving dots, as well as the Gabor patch spatial frequency, varies preferably in the same way in both first and second tasks. With reference to FIG. 14, the ratio RCDM of coherently moving dots in a display, within a same session, starts at a first value $C_0$ determined according to the individual's results obtained during the evaluation process (displays of FIGS. 3 to 8). The ratio of coherent dots motion is lowered from a test to another until an end value $C_f$, with, for example: $C_f = \frac{1}{3} (C_0 - 0.001)$, where:

$C_0$ is the initial RCDM value, during the first test, and $C_f$ is the final RCDM value, during the last test of the session.

The progression of the RCDM from the first to the last test within a same session can be linear as shown in FIG. 14.

The spatial frequency of the Gabor patches sf is increased from a session to another (as shown by dashed lines in FIG. 14) and is constant within a same session. The increase of the spatial frequency is constant, of a value $\Delta$ as shown, except for starting session 4 in the example shown in FIG. 14, where the step value is $+2\Delta$.

Thus, the training system can be advantageously a software-based, interactive system tailored and continuously adaptive to the individual patient's learning and improvement. The Internet can be used as a distribution media, which allows providing this personalized interactive service to a practically unlimited number of training locations, through the server 15 of FIG. 1. During each training session, the individual can be exposed to visual images displayed with moving patterns on a computer monitor. The patient can interactively communicate with the computer using for example a mouse or a keyboard. During each session, some data that reflects patient's performance can be recorded. At the end of the session, these data can be sent to the central server 15. Algorithmic software, running on the server, can analyze the patient's performance and progress and can generate the parameters for the next training session.

At least two types of progress calculations can be carried out in an implementation of the invention.

Figure 15:
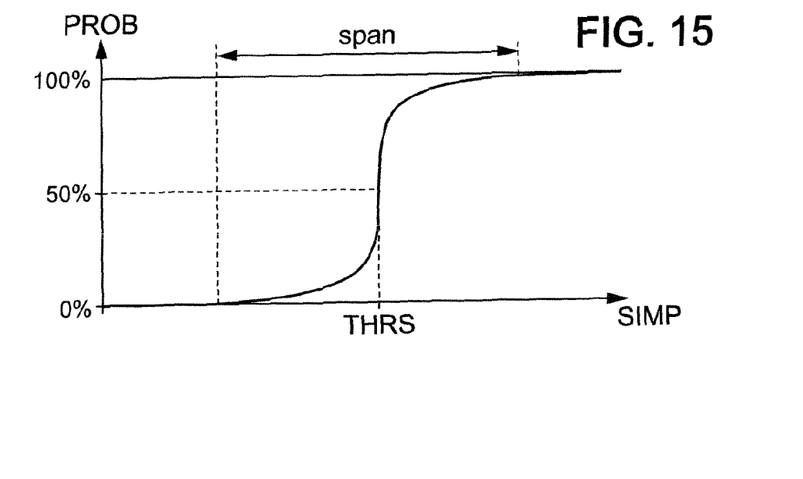
FIG. 15 shows an example of representation of the results obtained on an individual.

With reference to FIG. 15, a probability PROB of the subject to give a good answer to a test, versus simplicity SIMP, can be determined, on the basis of results in the DVP evaluation, for each task (with eye tracking, without eye tracking, detection of a coherent dots motion).

The variation of the probability PROB is represented by an increasing function comprising:

a first asymptote of zero value probability of good answers given at a test simplicity parameter SIMP below a threshold value THRS which can correspond for example to the final simplicity Simp found at the end of a staircase (steps S5 and S10 of FIG. 4), and a second asymptote of 100% value probability of good answers given at a test simplicity parameter greater than the test simplicity parameter threshold THRS.

Such a function can be a 5 degrees polynomial fit determined on the basis of the experimental results performed on a same subject.

Figure 16:
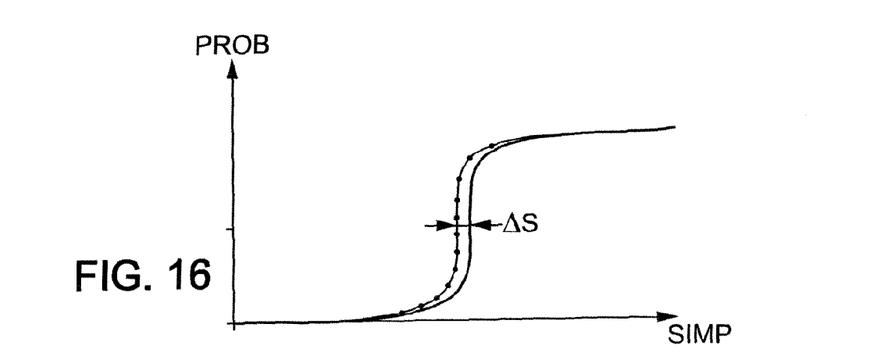
FIG. 16 shows a parameter ΔS based of a simplicity threshold difference and which can be used to calculate the individual's DVP improvement.

With reference to FIG. 16, the improvement of the individual's DVP can be calculated on the basis of the parameter $\Delta S$ aiming a difference between the threshold THRS measured before the training sessions (curve shown with solid line) and the threshold THRS measured after the training sessions (curve shown with dotted line).

Figure 17:
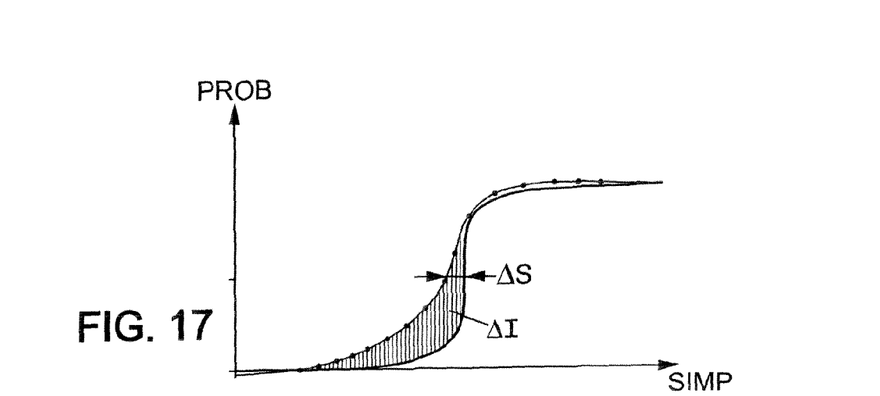
FIG. 17 shows a parameter ΔI based of an integral value difference and which can be used also to calculate the individual's DVP improvement.

Another parameter useful for quantifying the improvement of the individual's DVP is the integral of the function shown on FIG. 15. Indeed, with reference to FIG. 17, even if the value of parameter $\Delta S$ is small, the difference between the integral values of the curve shown with solid line (before the training sessions) and of the curve shown with dotted line (after the training sessions) assesses a strong improvement of the individual's DVP: even if the individual has not substantially increased his perception threshold, he had however increased his probability to detect moving stimuli below his perception threshold, with a satisfactory insurance. Therefore, the difference of integral values (noted $\Delta I$ on FIG. 17) is also an advantageous parameter quantifying the improvement of the individual's DVP. Practically, the integral value difference $\Delta I$ can be calculated in the span shown in FIG. 15.

Figure 18:
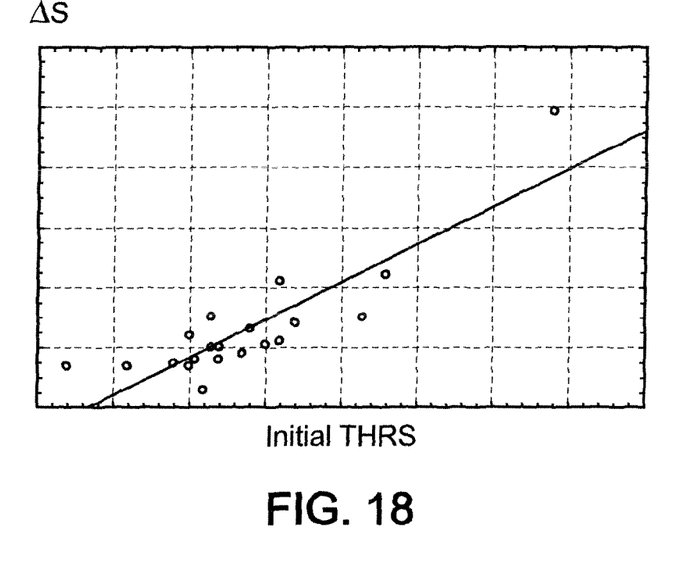
FIG. 18 shows a variation of the parameter ΔS quantifying a DVP improvement for several individuals, versus their initial DVP level obtained by implementing the evaluation method of the invention.

With reference to FIG. 18 showing a variation of $\Delta S$ parameter values of several subjects versus their initial threshold value THRS before their training sessions, it has been observed that the bigger the initial DVP of an individual is and the more it can be improved. Therefore, the DVP of an individual can be improved, even better if his DVP level is initially high. It will be thus understood that the improving method of the invention cannot be considered as a therapeutic method since its application is more suitable to subjects having initially a good DVP level (such as airplane pilots or high level sportsmen, for example). For example, it has been observed that the DVP of emmetrope subjects could be much more increased than the DVP of myope (shortsighted) subjects, in particular for the task of recognition of a pattern with eye tracking and identification of a coherent dots motion. Results of myope and emmetrope subjects were equivalent for the recognition of a pattern without eye tracking. Both methods of calculation based on the $\Delta S$ parameter value, on the one hand, and on the $\Delta I$ parameter value, on the other hand, gave substantially the same results.

Of course, the training sessions can be carried out for each eye of the individual, in order to improve selectively the dynamic visual perception of each eye. To that end, a flap can be provided to hide the inoperative eye of the individual, in the installation shown on FIG. 2.

The invention claimed is:

1. A method implemented by computer means, for evaluating a dynamic visual perception of an individual, comprising the steps of:

a) displaying on a screen at least one moving pattern having a chosen visual complexity feature, said pattern being selected amongst a plurality of possible patterns having each a value;

b) providing a human/machine interface enabling the individual to input a value to indicate the pattern that the individual sees on the screen;

c) receiving through said human/machine interface the inputted value and comparing said inputted value to the value of the displayed pattern;

d) repeating the preceding steps in order to count the number of successive positive comparisons at step c); and d1) if the number of successive positive comparisons exceeds a predetermined threshold, increasing said pattern visual complexity feature of a chosen amount, d2) otherwise, lowering said pattern visual complexity feature of a chosen amount; and e) repeating step d) and lowering said chosen amount each time an alternation between steps d1) and d2) is detected, until a predetermined number of alternations is detected, in order to determine a maximum visual complexity feature of patterns that the individual can identify, said maximum visual complexity feature defining a quantitative value of the dynamic visual perception of the individual.

2. The method according to claim 1 wherein the evaluation of said dynamic visual perception of the individual is based on at least one element amongst:

an ability to identify a moving pattern with eye tracking,
an ability to identify a moving pattern without eye tracking,
an ability to identify a global movement of a plurality of moving patterns,
an ability to read a chosen text displayed on the screen.

3. The method according to claim 1, wherein displayed patterns include alphabetic letters to recognize, and said pattern visual complexity feature comprises a global size of said alphabetic letters.

4. The method according to claim 1, wherein displayed patterns include Gabor patches having several possible orientations to recognize, and wherein said pattern visual complexity feature is defined by an amplitude of a Gabor function assigned to said patches.

5. The method according to claim 4, wherein randomly moving dots are further displayed on the screen in order to increase visual complexity.

6. The method according to claim 1, wherein the evaluation of said dynamic visual perception of the individual is based on an ability to identify a moving pattern with eye tracking,
wherein for evaluating said ability to identify a moving pattern with eye tracking, the individual is asked to:
follow the pattern on the screen while the pattern moves randomly from a position of the screen to another a predetermined number of times, and
input through said interface the value of the randomly moving pattern.

7. The method according to claim 1, wherein a fixed pattern is further displayed on the screen, and the individual is asked to stare at the fixed pattern while first and second patterns are displayed and move towards opposite directions on both sides of the fixed pattern,
and wherein the individual is asked to input through said interface at least one value of said first and second moving patterns, in order to test the individual's ability to identify a moving pattern without eye tracking.

8. The method according to claim 1, wherein a plurality of same moving patterns are displayed on the screen and a predetermined proportion of said same patterns move towards a same direction,
and wherein the individual is asked to determine through said interface whether at least some of the moving patterns move in a same direction or not, in order to test an ability to identify a global movement of a plurality of moving patterns.

9. The method according to claim 8, wherein said pattern visual complexity is defined by a complementary value of said proportion of patterns moving in a same direction.

10. A non-transitory computer readable storage medium, having stored thereon a computer product adapted to be stored in a memory of a processor unit, or in a removable memory medium adapted to cooperate with a reader of the processor unit, and/or downloadable from a distant website through an extended network to a data-processing unit, comprising instructions, the computer program being loadable into a data-processing unit and adapted to cause the data-processing unit to carry out, when the computer program is run by the data-processing device:
a) displaying on a screen at least one moving pattern having a chosen visual complexity feature, said pattern being selected amongst a plurality of possible patterns having each a value;
b) providing a human/machine interface enabling the individual to input a value to indicate the pattern that the individual sees on the screen,
c) receiving through said human/machine interface the inputted value and comparing said inputted value to the value of the displayed pattern,
d) repeating the preceding steps in order to count the number of successive positive comparisons at step c), and
d1) if the number of successive positive comparisons exceeds a predetermined threshold, increasing said pattern visual complexity feature of a chosen amount,
d2) otherwise, lowering said pattern visual complexity feature of a chosen amount,
e) repeating step d) and lowering said chosen amount each time an alternation between steps d1) and d2) is detected, until a predetermined number of alternations is detected, in order to determine a maximum visual complexity feature of patterns that the individual can identify, said maximum visual complexity feature defining a quantitative value of the dynamic visual perception of the individual.

11. A computer system for evaluating a dynamic visual perception of an individual, comprising means for performing the method according to claim 1.

12. A method implemented by computer means, for improving a dynamic visual perception of an individual, comprising a step of displaying on a screen at least one moving pattern having a chosen visual complexity feature, said pattern being selected amongst a plurality of predetermined patterns, the method further comprising an evaluation of said dynamic visual perception of the individual for improving said perception, the evaluation being carried according to the method as defined in claim 1.

13. The method according to claim 12, wherein step e) of the evaluation is carried out several times to observe an increase of said pattern maximum visual complexity on said individual, said increase ($\Delta S$) defining an improvement of the individual's dynamic visual perception.

14. The method according to claim 12, wherein an increasing function of an amount of individual good answers probability versus a test simplicity parameter is determined, said function comprising:
a first asymptote of zero value probability of good answers given at a test simplicity parameter below a threshold value corresponding substantially to said pattern maximum visual complexity, and
a second asymptote of 100% value probability of good answers given at a test simplicity parameter greater than said test simplicity parameter threshold,
wherein an integral value of said function is calculated, and
wherein step e) of the evaluation method is carried out several times to observe an increase of said integral value on said individual, said integral value increase ($\Delta I$) defining an improvement of the individual's dynamic visual perception.

15. The method according to claim 12, wherein the method is carried out on at least one individual's eye in order to improve selectively the dynamic visual perception of said individual's eye.

16. A non-transitory computer readable storage medium, having stored thereon a computer program adapted to be stored in a memory of a processor unit, or in a removable memory medium adapted to cooperate with a reader of the processor unit, and/or downloadable from a distant website through an extended network to a data-processing unit, comprising instructions, the computer program being loadable into a data-processing unit and adapted to cause the data-processing unit to carry out, when the computer program is run by the data-processing device, for improving a dynamic visual perception of an individual:

displaying on a screen at least one moving pattern having a chosen visual complexity feature, said pattern being selected amongst a plurality of predetermined patterns, the computer program being adapted to cause the data-processing unit to carry out an evaluation of said dynamic visual perception of the individual for improving said perception, the evaluation being carried according to the method as defined in claim 1.

17. A computer system for improving a dynamic visual perception of an individual, comprising means for performing the method according to claim 12.

* * * * *